United States Patent
Hathaway et al.

(10) Patent No.: US 9,192,295 B1
(45) Date of Patent: Nov. 24, 2015

(54) FOCUSING ALGORITHM IN OCT-ONLY SYSTEMS

(71) Applicant: L&R Medical Inc., Toronto (CA)

(72) Inventors: Mark Hathaway, Canterbury (GB); Rishard Weitz, Toronto (CA)

(73) Assignee: L&R MEDICAL INC., Toronto, Ontario (CA)

( * ) Notice: Subject to any disclaimer, the term of this patent is extended or adjusted under 35 U.S.C. 154(b) by 0 days.

(21) Appl. No.: 14/301,626

(22) Filed: Jun. 11, 2014

(51) Int. Cl.
- *A61B 3/10* (2006.01)
- *G02B 7/36* (2006.01)
- *A61B 3/12* (2006.01)

(52) U.S. Cl.
CPC ............... *A61B 3/102* (2013.01); *A61B 3/1225* (2013.01); *G02B 7/36* (2013.01)

(58) Field of Classification Search
CPC ........................................................ A61B 3/102
USPC ................................. 351/205, 206, 208, 210
See application file for complete search history.

(56) References Cited

U.S. PATENT DOCUMENTS

| | | |
|---|---|---|
| 5,493,109 A | 2/1996 | Wei et al. |
| 8,204,300 B2 | 6/2012 | Sugita et al. |
| 8,842,287 B2 | 9/2014 | Yazdanfar et al. |
| 8,939,582 B1 | 1/2015 | Spaide et al. |
| 8,970,846 B2 | 3/2015 | Kubota et al. |
| 2011/0149245 A1* | 6/2011 | Barth et al. .................... 351/215 |
| 2011/0279821 A1* | 11/2011 | Brennan et al. ................ 356/479 |
| 2012/0106937 A1 | 5/2012 | Molin et al. |
| 2012/0257212 A1 | 10/2012 | Okikawa et al. |
| 2013/0169971 A1 | 7/2013 | Brown et al. |

FOREIGN PATENT DOCUMENTS

| | | |
|---|---|---|
| WO | 2007091991 A2 | 8/2007 |
| WO | 2013083147 A1 | 6/2013 |

* cited by examiner

*Primary Examiner* — Huy K Mai

(74) *Attorney, Agent, or Firm* — Marks & Clerk; S. Mark Budd

(57) ABSTRACT

In an OCT system, the autocorrelation signal depends only on the strength of the signal in the object arm scattered back from a patient's retina and is a result of different reflections from different layers of the retina interfering with each other. The strength of the autocorrelation signal depends on how well focused the system is. Normally the autocorrelation signal is treated as noise. However by removing the reference path signal, the autocorrelation signal is easily measured and analyzed. The optimal focus can the then be found by adjusting the focus value until the autocorrelation signal is maximized.

17 Claims, 1 Drawing Sheet

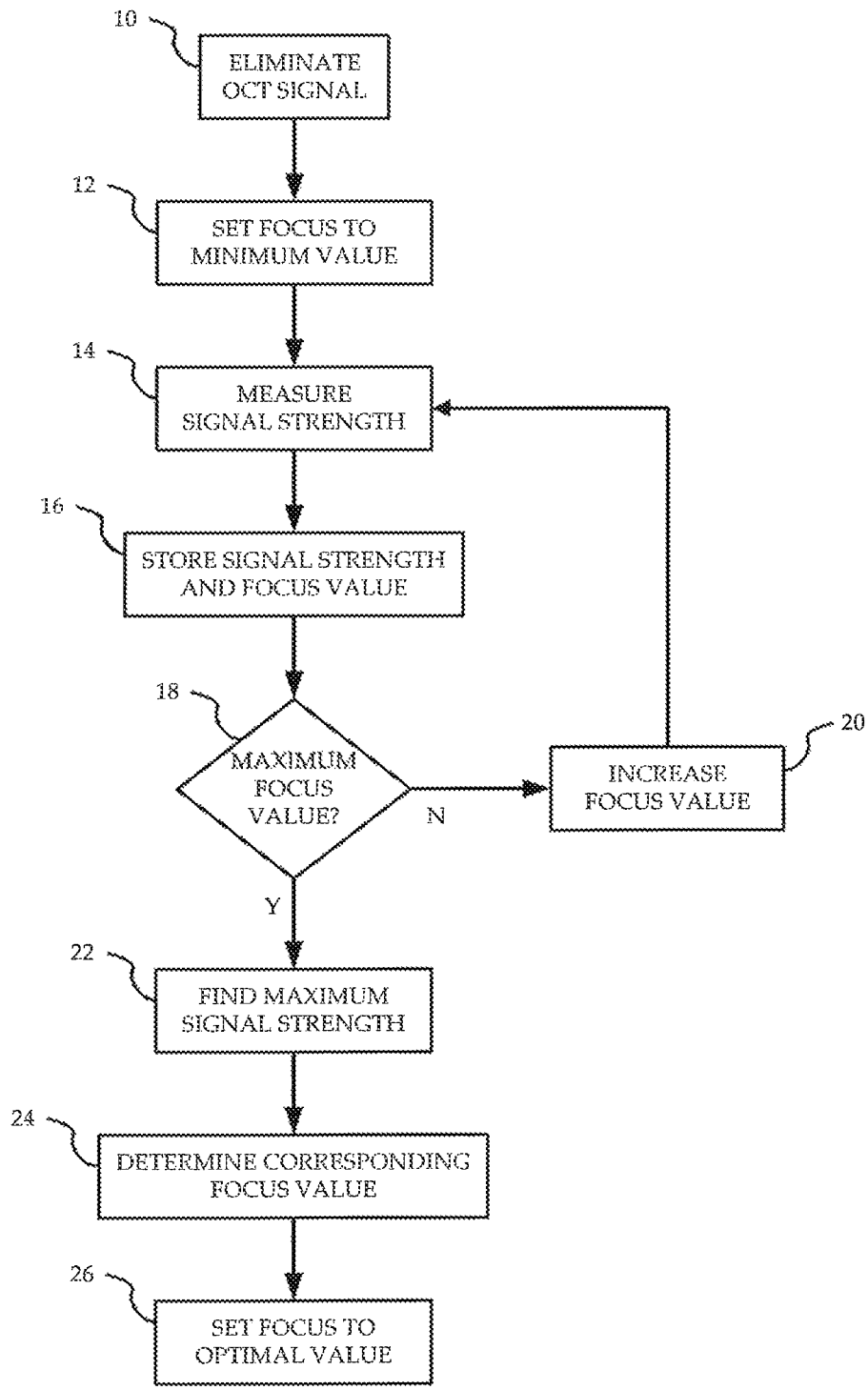

FOCUSING ALGORITHM IN OCT-ONLY SYSTEMS

FIELD OF INVENTION

This invention relates to a method of focusing on the retina in ophthalmology, and in particular to focusing on the retina in systems which employ only OCT.

BACKGROUND

Most optical coherence tomography (OCT) systems provide either a fundus camera or a scanning laser ophthalmoscopy (SLO) channel in order to provide a 2D image of the retina, in addition to the usual OCT data. This image is usually used for alignment and for focus optimization. In an OCT-only system, i.e. without also having a SLO system or fundus camera, an SLO signal can be synthesized from the OCT signal if a 3D volume is acquired, so a 2D fundus image can still be produced.

However, in order to optimize the focus using the OCT signal, the reference path of the interferometer must be correctly matched with the object path to the patient's retina. In a spectral OCT system, light from a single source is split into two parts which traverse different paths in an interferometer. One path, the reference path, simply introduces a variable delay into the beam. The other path, called the object path, includes a patient's eye. Light scattered back from the patient's eye is mixed with light from the reference path to produce an interference signal. The interference signal is then analyzed with a spectrometer.

For an effective OCT signal to be produced the two paths must be matched in length, which is the reason for the reference path length being variable. However this can be difficult due to patient movement. If the focus is not closely matched to the patient in the first place, then the OCT signal can be very difficult to detect. The focus adjustment and the reference path adjustments have to be controlled together. The coupling of these two parameters can make it very difficult to achieve optimal focus, especially when the patient has a high diopter prescription.

There is a need to provide a method of achieving optimal focus which decouples the focus adjustment and the reference arm adjustment.

SUMMARY

According to one aspect, a method of focusing a spectral optical coherence tomography (OCT) system is provided. An OCT signal that is caused by interference between a beam in the reference arm of the OCT system and a beam in the object arm of the OCT system is eliminated. The focus of the OCT system is set at a variety of values, and for each focus value, the signal strength of a beam reflected from a patient's eye is measured and stored in association with the focus value. A maximum of the stored signal strengths is determined. An optimal focus value is determined as the focus value stored in association with the maximum of the stored signal strengths. The focus of the OCT system is set to the optimal focus value.

The methods of the invention may be stored as logical instructions on a non-transitory computer-readable storage medium in a form executable by a computer processor.

The autocorrelation signal depends only on the strength of the signal reflected back from a patient's eye in the object arm. By removing the reference path signal, the autocorrelation signal is more easily measured and analyzed. The strength of the autocorrelation signal depends on how well focused the system is, and the optimal focus can therefore be found by adjusting the focus value until the autocorrelation signal is maximized. Movement by the patient is also not a complication in determining the optimal focus using only the autocorrelation signal, since the reference path is omitted and hence there is no need to match path lengths.

BRIEF DESCRIPTION OF THE DRAWINGS

The features and advantages of embodiments of the invention will become more apparent from the following detailed description of the preferred embodiment(s) with reference to the attached figures, wherein:

FIG. 1 is a flowchart of a method of determining optimal focus in an OCT system according to one embodiment of the invention.

It is noted that in the attached figures, like features bear similar labels.

DETAILED DESCRIPTION OF THE PREFERRED EMBODIMENTS

The autocorrelation signal of a beam of light reflected by a patient's eye is produced by different reflections of the beam, reflecting off different layers of the retina, interfering with each other. The autocorrelation signal is therefore always present and does not require interference with the reference beam. It is present solely in the returned object beam. Usually the autocorrelation signal is considered noise in OCT systems. OCT systems are normally designed to suppress the autocorrelation signal relative to the OCT signal by suitable choice of reference beam power. This is possible because the OCT signal is a function of the reference beam power and the object beam power, whereas the autocorrelation signal is a function only of the object beam power.

The optimum focus can be determined by simply measuring the signal strength of the autocorrelation signal. Broadly, an OCT signal that is caused by interference between a beam in a reference arm of the OCT system and a beam in an object arm of the OCT system is eliminated. The focus of the OCT system is set at a variety of values, and for each focus value the signal strength of a beam reflected from a patient's eye is measured. This is stored in association with the focus value at which the measurement was made. After measuring the signal strength at the variety of focus values, the maximum of the stored signal strengths is determined, and the optimal focus value is that stored in association with the maximum of the stored signal strengths. The focus of the OCT system is then set to this optimal focus value.

Referring to FIG. 1, a flowchart of a method of determining optimal focus in an OCT system according to one embodiment of the invention is shown. The method is preferably executed by a processor which can take as an input from the spectrometer of an OCT system a signal strength at a selectable frequency. The processor can preferably also adjust the focus control of the OCT system, in order to fully automate the method of the invention.

At step 10 the OCT signal is eliminated, so that the only signal reaching the spectrometer of the OCT system is the autocorrelation signal. The OCT signal is most easily eliminated by setting the reference path to an extreme position, such as at a maximum or a minimum length, resulting in no interference between the reference beam and the reflected beam within the object path. However other means of eliminating an OCT signal may be used, such as by attenuating the reference arm power. At step 12 the focus control of the OCT system is set to the minimum value of the focus.

At step 14 the signal strength of the signal reaching the spectrometer of the OCT system is measured. Normally this signal would result from interference between a signal in the reference arm and a signal in the object arm, the latter being reflected from the patient's retina. However since the OCT signal has been eliminated at step 10, such as by extending the reference path to an extreme position, the only signal received by the spectrometer is the reflected beam within the object arm and the autocorrelation signal is visible as more than just noise. The signal strength is measured by integrating the signal over the frequency range of the spectrum, the spectrometer having performed a Fourier transform (preferably a Fast Fourier Transform) on the signal.

At step 16 the signal strength and the focus value are stored in association with each other. At step 18 the processor determines whether the maximum focus value has been reached. If the maximum focus value has not been reached, then at step 20 the focus value is increased. Any step size can be used in increasing the focus value, most OCT systems having extremely fine control of the focusing element. However most of the time a resolution of 0.25 Diopter is sufficient for achieving good focus and a step size of 0.25 Diopter may be adequate.

Eventually the maximum focus value is reached, and at step 22 processor determines the maximum of the signal strengths that were stored at step 16. Once this maximum of the signal strengths is determined, then at step 24 the processor determines the focus value that is stored in association with the maximum of the signal strengths. This focus value is the optimal focus value, and in a fully automated system the processor then sets the focus value of the OCT system at step 26 to the optimal focus value. Alternatively, the processor simply causes the optimal focus value to be displayed, and the focus of the OCT system is set manually to this optimal focus value.

The steps 14, 18, and 20 together form a loop which causes the processor to measure the signal strength at a variety of focus values over the range of possible focus values. Other means of measuring the signal strength at a variety of focus values can be used, such as starting at the maximum possible focus value and measuring the signal strength at successively smaller focus values. In one embodiment, the variety of focus values at which the signal strength is measured is a subset of the entire range of possible focus values. Such an embodiment may be used, for example, if a rough idea of the optimal focus value is known.

The logic of the methods described above may be stored as instructions stored on anon-transitory computer-readable storage medium in a form executable by a computer processor, although either eliminating the OCT signal or setting the focus of the OCT system to the optimal focus value, or both, may be carried out manually instead. The processor may be implemented by a general purpose processor, a network processor, a digital signal processor, an ASIC, or multiple such devices.

The embodiments presented are exemplary only and persons skilled in the art would appreciate that variations to the embodiments described above may be made without departing from the spirit of the invention. The scope of the invention is solely defined by the appended claims.

We claim:

1. A method of focusing a spectral optical coherence tomography (OCT) system, comprising:
    eliminating an OCT signal that is caused by interference between a beam in a reference arm of the OCT system and a beam in an object arm of the OCT system;
    setting a focus of the OCT system at a variety of values;
    for each focus value, measuring the signal strength of a beam reflected from a patient's eye, and storing the measured signal strength and the focus value is association with each other;
    determining a maximum of the stored signal strengths;
    determining as an optimal focus value the focus value stored in association with the maximum of the stored signal strengths; and
    setting the focus of the OCT system to the optimal focus value.

2. The method of claim 1 wherein eliminating the OCT signal comprises setting the reference arm at an extreme position.

3. The method of claim 1 wherein eliminating the OCT signal comprises attenuating the power of the beam in the reference arm.

4. The method of claim 1 wherein measuring the signal strength of a beam reflected from a patient's eye comprises integrating the strength of the signal over a range of frequencies in the signal.

5. The method of claim 4 wherein eliminating the OCT signal comprises setting the reference arm at an extreme position.

6. The method of claim 4 wherein eliminating the OCT signal comprises attenuating the power of the beam in the reference arm.

7. The method of claim 1 wherein setting a focus of the system at a variety of values comprises:
    setting the focus of the OCT system at a minimum focus value;
    increasing the focus of the OCT system in steps until the maximum focus value is reached.

8. The method of claim 7 wherein measuring the signal strength of a beam reflected from a patient's eye comprises integrating the strength of the signal over a range of frequencies in the signal, and wherein eliminating the OCT signal comprises setting the reference arm at an extreme position.

9. A non-transitory computer-readable medium comprising instructions executable by a computer processor for focusing a spectral optical coherence tomography (OCT) system, the instructions comprising instructions to:
    set a focus of the OCT system at a variety of values;
    for each focus value, measure the signal strength of a beam reflected from a patient's eye, and store the measured signal strength and the focus value is association with each other;
    determine a maximum of the stored signal strengths; and
    determine as an optimal focus value the focus value stored in association with the maximum of the stored signal strengths.

10. The non-transitory computer-readable medium of claim 9, further comprising instructions to eliminate an OCT signal that is caused by interference between a beam in a reference arm of the OCT system and a beam in an object arm of the OCT system.

11. The non-transitory computer-readable medium of claim 10 wherein the instructions to eliminate the OCT signal comprise instructions to set the reference arm to an extreme position.

12. The non-transitory computer-readable medium of claim 10 wherein the instructions to eliminate the OCT signal comprise instructions to attenuate the power of the beam in the reference arm.

13. The non-transitory computer-readable medium of claim 9, further comprising instructions to set the focus of the OCT system to the optimal focus value.

14. The non-transitory computer-readable medium of claim 9 wherein the instructions to measure the signal strength of a beam reflected from a patient's eye comprise instructions to integrate the strength of the signal over a range of frequencies in the signal.

15. The non-transitory computer-readable medium of claim 9 further comprising:
   instructions to eliminate an OCT signal that is caused by interference between a beam in a reference arm of the OCT system and a beam in an object arm of the OCT system; and
   instructions to set the focus of the OCT system to the optimal focus value,
and wherein the instructions to measure the signal strength of a beam reflected from a patient's eye comprise instructions to integrate the strength of the signal over a range of frequencies in the signal.

16. The non-transitory computer-readable medium of claim 15 wherein the instructions to eliminate the OCT signal comprise instructions to set the reference arm to an extreme position.

17. The non-transitory computer-readable medium of claim 15 wherein the instructions to eliminate the OCT signal comprise instructions to attenuate the power of the beam in the reference arm.

* * * * *